(12) United States Patent
Eto et al.

(10) Patent No.: US 11,513,107 B2
(45) Date of Patent: Nov. 29, 2022

(54) GAS FEATURE VECTOR DECOMPOSITION

(71) Applicant: NEC Corporation, Tokyo (JP)

(72) Inventors: Riki Eto, Tokyo (JP); Hiromi Shimizu, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 17/294,146

(22) PCT Filed: Nov. 16, 2018

(86) PCT No.: PCT/JP2018/042465
§ 371 (c)(1),
(2) Date: May 14, 2021

(87) PCT Pub. No.: WO2020/100285
PCT Pub. Date: May 22, 2020

(65) Prior Publication Data
US 2022/0018823 A1  Jan. 20, 2022

(51) Int. Cl.
*G01N 33/00* (2006.01)
(52) U.S. Cl.
CPC .................... *G01N 33/0027* (2013.01)
(58) Field of Classification Search
CPC .... G01N 19/00; G01N 27/12; G01N 33/0027; G01N 5/02; G01N 33/0004; G01N 2033/0068
See application file for complete search history.

(56) References Cited

U.S. PATENT DOCUMENTS

| | | | | |
|---|---|---|---|---|
| 2010/0024533 A1* | 2/2010 | Kimura | ................... | G01N 5/02 73/73 |
| 2017/0160221 A1* | 6/2017 | Savoy | ................ | G01N 33/0008 |

FOREIGN PATENT DOCUMENTS

| | | | |
|---|---|---|---|
| JP | H11-264809 A | | 9/1999 |
| JP | 2016050995 | * | 4/2016 |
| JP | 2017-156254 A | | 9/2017 |
| WO | 2008/126519 A1 | | 10/2008 |

OTHER PUBLICATIONS

Nakamoto et al, "Odor Approximation Using Mass Spectrometry", IEEE Sensors Journal, vol. 12, No. 11, (2012).*
International Search Report for PCT Application No. PCT/JP2018/042465, dated Jan. 15, 2019.
S. Seto et al., "Chemical Analysis for Transient Response of Semiconductor Sensor by Autoregressive Model", IEEJ Transactions on Sensors and Micromachines, vol. 125, No. 3, 2005, pp. 129-134.
H. Kameoka, "Non-Negative Matrix Factorization", Journal of the Society of Instrument and Control Engineers, vol. 51, No. 9, Sep. 2012, pp. 835-844.

* cited by examiner

*Primary Examiner* — Catherine T. Rastovski

(57) ABSTRACT

An information processing apparatus (2000) acquires a feature vector (20) obtained based on signal data (14) of a detected value of a sensor (10) that senses gas to be measured. The information processing apparatus (2000) decomposes the feature vector (20) into a product of a coefficient vector and a feature matrix by using a non-negative matrix factorization (NMF). The detected value of the sensor (10) changes according to an attachment and a detachment of a molecule contained in a sensed gas. A value of each element of the feature vector (20) is equal to or greater than zero.

14 Claims, 11 Drawing Sheets

GAS FEATURE VECTOR DECOMPOSITION

This application is a National Stage Entry of PCT/JP2018/042465 filed on Nov. 16, 2018, the contents of all of which are incorporated herein by reference, in their entirety.

TECHNICAL FIELD

The present invention relates to an analysis of a feature of gas.

BACKGROUND ART

A technique has been developed to obtain information related to gas by measuring the gas with a sensor. Patent Document 1 discloses a technique for discriminating the type of sample gas by using a signal (time-series data of detected values) obtained by measuring the sample gas with a nanomechanical sensor. Specifically, since a diffusion time constant of the sample gas with respect to a receptor of the sensor is determined by a combination of the type of the receptor and the type of the sample gas, it is disclosed that the type of the sample gas can be discriminated based on the diffusion time constant obtained from the signal and the type of the receptor.

RELATED DOCUMENT

Patent Document

[Patent Document 1] Japanese Patent Application Publication No. 2017-156254

SUMMARY OF THE INVENTION

Technical Problem

In Patent Document 1, it is assumed that one type of molecule is contained in the sample gas, and it is not assumed that the sample gas in which a plurality of types of components are mixed is handled. The present invention has been made in view of the above problems and is to provide a technique for extracting a feature of gas in which a plurality of types of molecules are mixed.

Solution to Problem

An information processing apparatus of the present invention includes: 1) an acquisition unit that acquires a feature vector of gas to be measured which is obtained based on signal data of a detected value of a sensor that senses the gas to be measured; and 2) a decomposition unit that decomposes the feature vector of the gas to be measured into a product of a vector and a matrix by using a non-negative matrix factorization (NMF). The detected value of the sensor changes according to an attachment and a detachment of a molecule contained in a sensed gas. A value of each element of the feature vector of the gas to be measured is equal to or greater than zero.

A control method of the present invention is executed by a computer. The control method includes: 1) an acquisition step of acquiring a feature vector of gas to be measured which is obtained based on signal data of a detected value of a sensor that senses the gas to be measured; and 2) a decomposition step of decomposing the feature vector of the gas to be measured into a product of a vector and a matrix by using a non-negative matrix factorization (NMF). The detected value of the sensor changes according to an attachment and a detachment of a molecule contained in a sensed gas. A value of each element of the feature vector of the gas to be measured is equal to or greater than zero.

A program of the present invention causes a computer to execute each step included in the control method of the present invention.

Advantageous Effects of Invention

According to the present invention, there is provided a technique for extracting a feature of gas in which a plurality of types of molecules are mixed.

BRIEF DESCRIPTION OF THE DRAWINGS

The above-described object, other objects, features, and advantages will be further clarified by the preferred example embodiments described below and the accompanying drawings.

DESCRIPTION OF EMBODIMENTS

Hereinafter, example embodiments of the present invention will be described with reference to the drawings. In all the drawings, the same constituents will be referred to with the same numerals, and the description thereof will not be repeated. Further, in each block diagram, each block represents a functional unit configuration, not a hardware unit configuration, unless otherwise specified.

Example Embodiment 1

<Outline of Invention>

Figure 1:
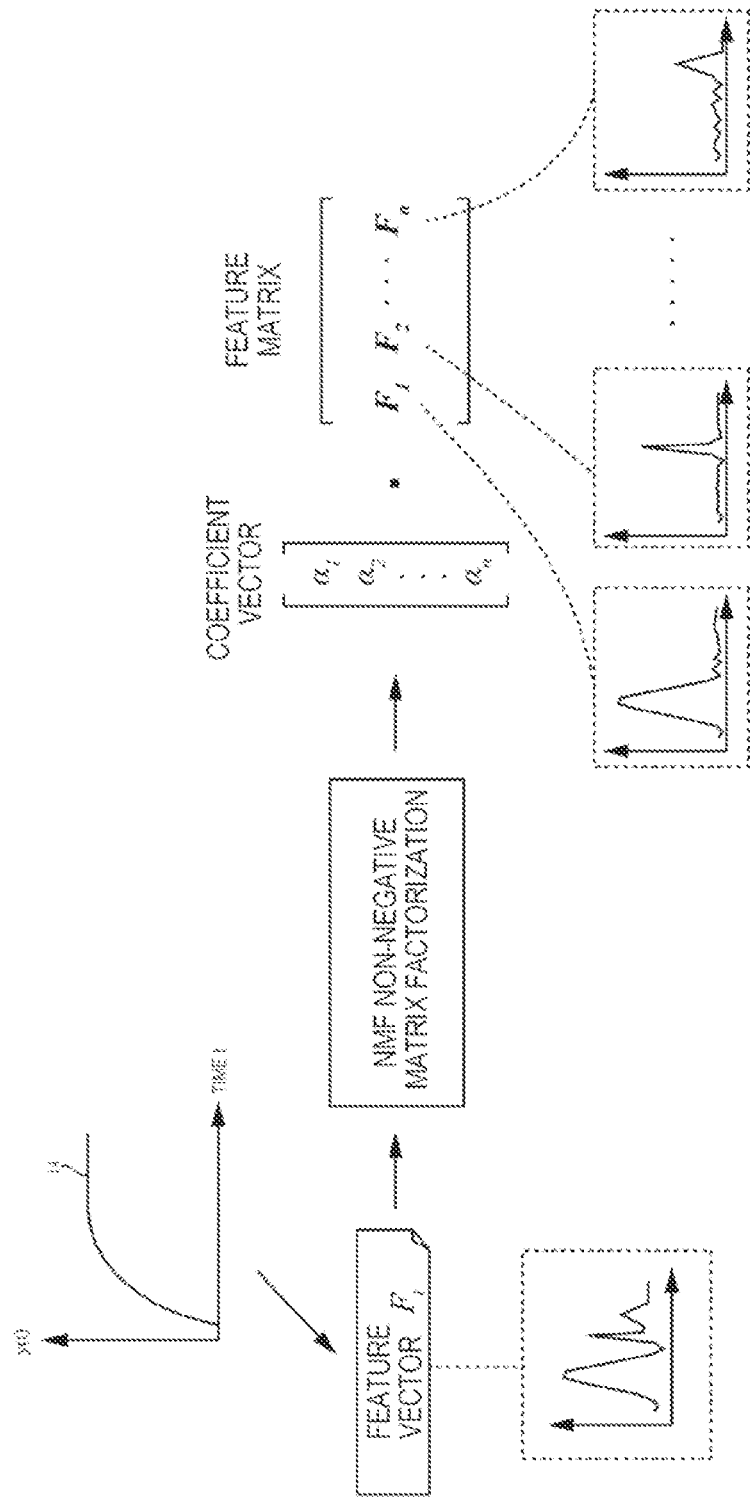
FIG. 1 is a diagram illustrating an outline of an information processing apparatus (an information processing apparatus in FIG. 3) according to Example Embodiment 1.
Figure 2:
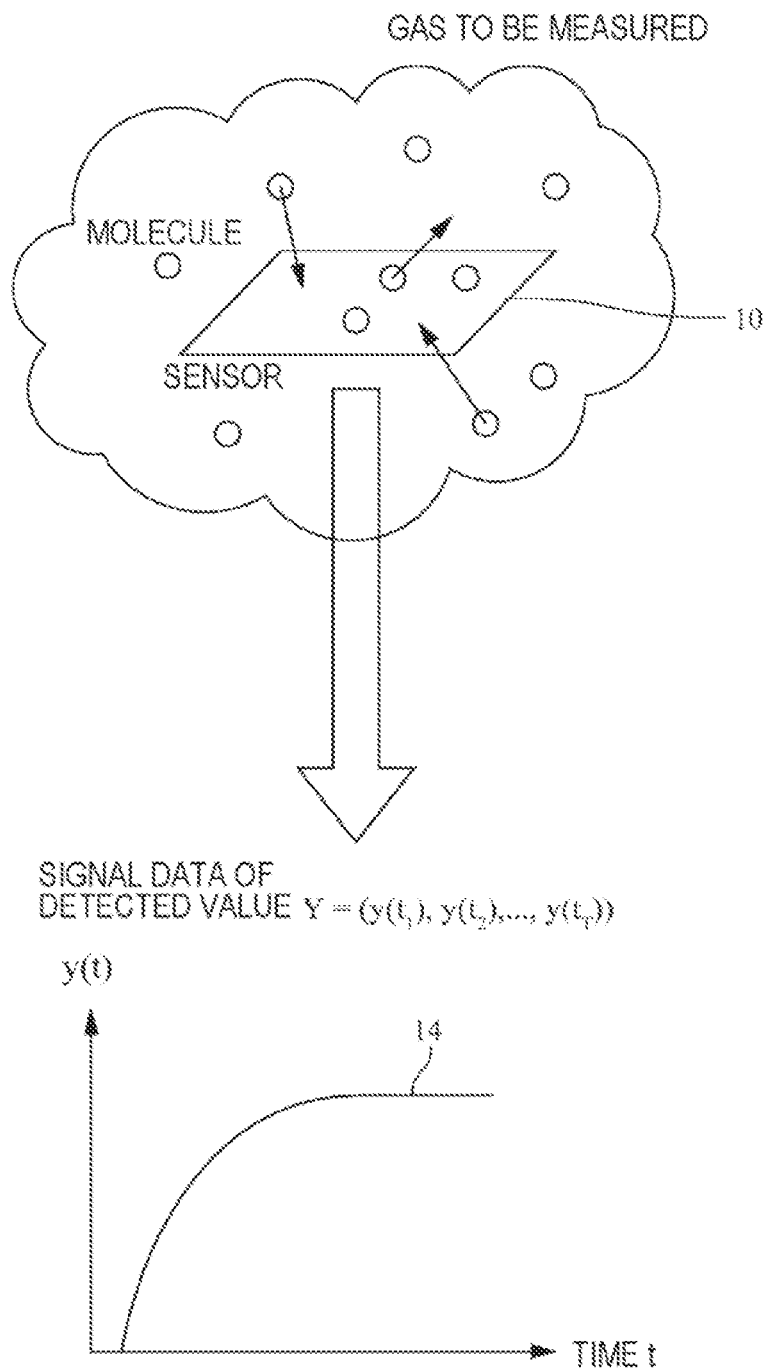
FIG. 2 is a diagram illustrating a sensor for obtaining data acquired by the information processing apparatus.

FIG. 1 is a diagram illustrating an outline of an information processing apparatus (an information processing apparatus 2000 in FIG. 3) according to Example Embodiment 1. Further, FIG. 2 is a diagram illustrating a sensor 10 for obtaining data acquired by the information processing apparatus 2000. The sensor 10 is a sensor that has a receptor to which a molecule is attached and the detected value of the sensor is changed according to attachment and detachment of the molecule at the receptor. The signal data (time-series data) of the detected value output from the sensor 10 in response to sensing the gas is referred to as signal data 14. Note that, when necessary, the signal data 14 is also expressed as a signal vector Y, and the detected value at time t is also expressed as y(t). Y is a vector in which y(t) is enumerated.

For example, the sensor 10 is a Membrane-type Surface Stress (MSS) sensor. The MSS sensor has a functional membrane to which a molecule is attached as a receptor, and stress generated in a supporting member of the functional membrane is changed due to the attachment and detachment of the molecule with respect to the functional membrane. The MSS sensor outputs the detected value based on the change in the stress. Note that, the sensor 10 is not limited to the MSS sensor, may be any sensor that outputs the detected value based on changes in physical quantities related to the viscoelasticity and dynamic characteristics (the mass, the moment of inertia, or the like) of a member of the sensor 10 that occur in response to the attachment and detachment of the molecule with respect to the receptor, and various types of sensors can be adopted such as a cantilever type, a membrane type, an optical type, a Piezo, and an oscillation response.

From the result of the measurement using the sensor 10, the feature vector of the component contained in the gas to be measured can be obtained, thereby the sensor 10 can also be called an "odor sensor". That is, when it is desired to recognize the feature of the odor emitted by a certain substance, the vapor generated from the substance (if the substance is gas, the gas itself) is measured by the sensor 10 and a feature vector based on the measurement result is obtained, and then the feature of the odor emitted by the substance can be recognized.

The information processing apparatus 2000 acquires the feature vector 20 obtained based on the signal data 14 obtained by sensing the gas to be measured with the sensor 10. It is assumed that the gas to be measured contains a plurality of molecules. The feature vector 20 represents the feature value of the gas to be measured by vector. For example, the feature vector 20 is spectral data representing the intensity of each frequency component included in the signal data 14. In this case, each element of the feature vector 20 corresponds to one frequency component, and the value of that element represents the magnitude of the frequency component. However, the feature vector 20 is not limited to the spectrum data of the frequency component. Details of the feature vector 20 will be described later.

When the gas to be measured contains a plurality of components, it is considered that the feature vector 20 representing the feature of the gas to be measured is a combination of the feature vectors of each of the plurality of components contained in the gas to be measured. In particular, when handling the feature value having linearity such as a frequency spectrum, the feature vector 20 can be represented by a conical combination of the respective feature vectors of components. In following Expression (1), the feature vector 20 is represented by a conical combination of the respective feature vectors of the plurality of components.

[Expression 1]

$$F_t = \sum_{1 \leq i \leq n} \alpha_i F_i \quad (1)$$

$$= \begin{pmatrix} \alpha_1 \\ \vdots \\ \alpha_n \end{pmatrix} (F_1 \ \ldots \ F_n)$$

Here, $F_t$ represents the feature vector 20, and $F_i$ represents the feature vector of each component i. Further, $\alpha_i$ represents the conical combination coefficient of component i in the gas to be measured. Note that, $\alpha_i \geq 0$. Further, when the total sum of $\alpha_i$ is set to 1, $\alpha_i$ represents the mixing ratio (concentration ratio).

Therefore, the information processing apparatus 2000 decomposes the feature vector 20 into a plurality of feature vectors by using a non-negative matrix factorization (NMF). More specifically, the information processing apparatus 2000 decomposes the feature vector 20 into a product of one vector representing the respective conical combination coefficients of the plurality of feature vectors and one matrix representing the plurality of feature vectors. Hereinafter, this vector and the matrix are referred to as a coefficient vector and a feature matrix, respectively. The coefficient vector corresponds to a vector in which $\alpha_i$ is enumerated in Expression (1). The feature matrix corresponds to a matrix in which the feature vector $F_i$ is enumerated in Expression (1).

In this way, by using the NMF, the feature vector 20 can be decomposed into conical combinations of a plurality of vectors. That is, with the information processing apparatus 2000, it is possible to obtain the feature of each of the plurality of components (single molecule or combination of a plurality of molecules) contained in the gas to be measured containing the plurality of molecules.

The information processing apparatus 2000 is particularly useful in a case where one or more components contained in the gas to be measured are unknown. This is because the NMF can be executed without prior knowledge of the matrix resulting from the execution thereof. For the same reason, it is particularly useful in a case where the components contained in the gas to be measured are known but the feature vector is unknown for one or more of the components.

Note that, the above description with reference to FIGS. 1 and 2 is an example for facilitating understanding of the information processing apparatus 2000 and does not limit the function of the information processing apparatus 2000. Hereinafter, the information processing apparatus 2000 of the present example embodiment will be described in more detail.

<Example of Functional Configuration>

Figure 3:
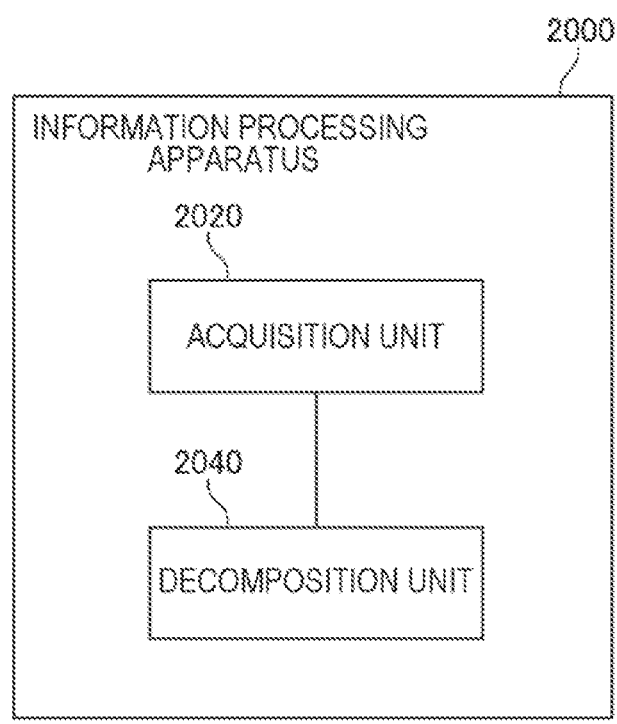
FIG. 3 is a diagram illustrating a functional configuration of the information processing apparatus according to Example Embodiment 1.

FIG. 3 is a diagram illustrating a functional configuration of the information processing apparatus 2000 according to Example Embodiment 1. The information processing apparatus 2000 of Example Embodiment 1 has an acquisition unit 2020 and a decomposition unit 2040. The acquisition unit 2020 acquires the feature vector 20 of the gas to be measured. The decomposition unit 2040 decomposes the feature vector 20 into the product of the coefficient vector and the feature matrix by executing the NMF on the feature vector 20 of the gas to be measured.

<Hardware Configuration of Information Processing Apparatus 2000>

Each functional configuration unit of the information processing apparatus 2000 may be implemented by hardware (for example, a hard-wired electronic circuit or the like) that implements each functional configuration unit, or may be implemented by a combination of hardware and software (for example, a combination of an electronic circuit and a program for controlling the electronic circuit). Hereinafter, a case where each functional configuration unit of the information processing apparatus 2000 is implemented by a combination of hardware and software will be further described.

Figure 4:
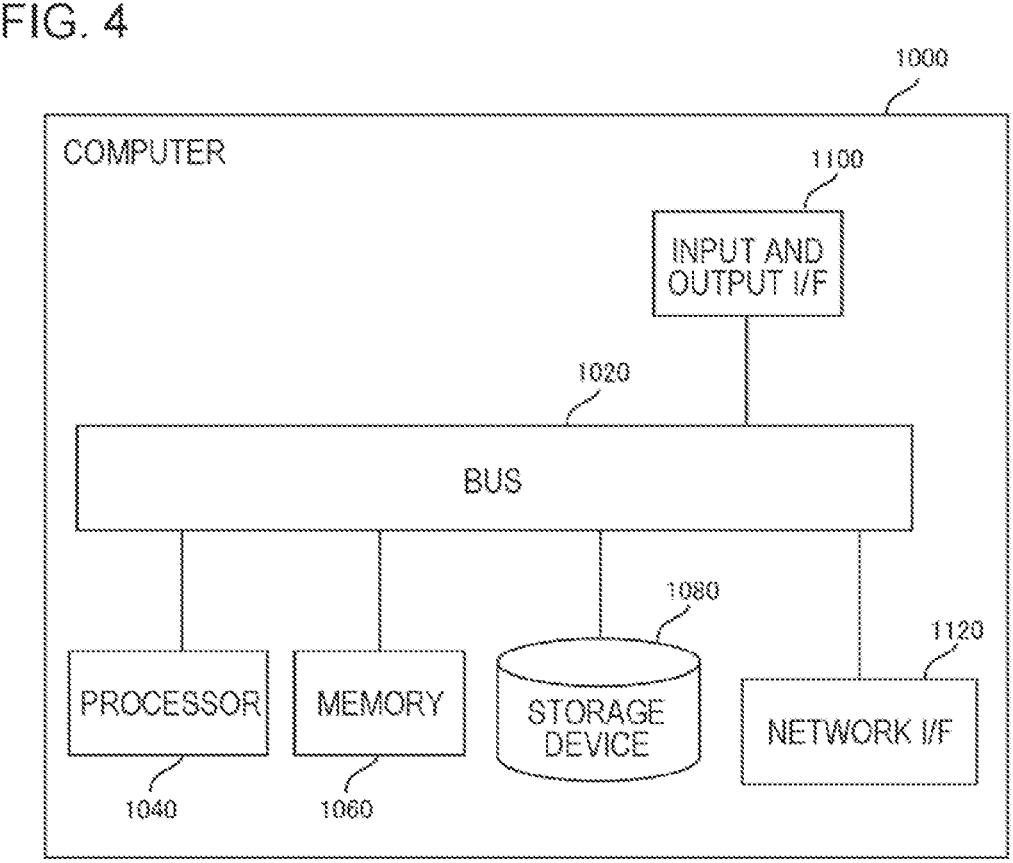
FIG. 4 is a diagram illustrating a computer for implementing the information processing apparatus.

FIG. 4 is a diagram illustrating a computer 1000 for implementing the information processing apparatus 2000. The computer 1000 is any computer. For example, the computer 1000 is a stationary computer such as a personal computer (PC) or a server machine. In addition, for example, the computer 1000 is a portable computer such as a smartphone or a tablet terminal. The computer 1000 may be a dedicated computer designed to implement the information processing apparatus 2000 or may be a general-purpose computer.

The computer 1000 includes a bus 1020, a processor 1040, a memory 1060, a storage device 1080, an input and output interface 1100, and a network interface 1120. The bus 1020 is a data transmission path for the processor 1040, the memory 1060, the storage device 1080, the input and output interface 1100, and the network interface 1120 to mutually transmit and receive data. However, the method of connecting the processors 1040 and the like to each other is not limited to the bus connection.

The processor 1040 is various processors such as a Central Processing Unit (CPU), a Graphics Processing Unit (GPU), and a Field-Programmable Gate Array (FPGA). The memory 1060 is a main storage device implemented by using a Random Access Memory (RAM) or the like. The storage device 1080 is an auxiliary storage device implemented by using a hard disk, a Solid State Drive (SSD), a memory card, a Read Only Memory (ROM), or the like.

The input and output interface 1100 is an interface for connecting the computer 1000 and the input and output devices. For example, an input device such as a keyboard or an output device such as a display device is connected to the input and output interface 1100.

The network interface 1120 is an interface for connecting the computer 1000 to a communication network. The communication network is, for example, a Local Area Network (LAN) or a Wide Area Network (WAN). A method of connecting the network interface 1120 to the communication network may be a wireless connection or a wired connection.

The storage device 1080 stores a program module that implements each functional configuration unit of the information processing apparatus 2000. The processor 1040 implements the function corresponding to each of these program modules by reading each program module into the memory 1060 and executing the modules.

<Process Flow>

Figure 5:
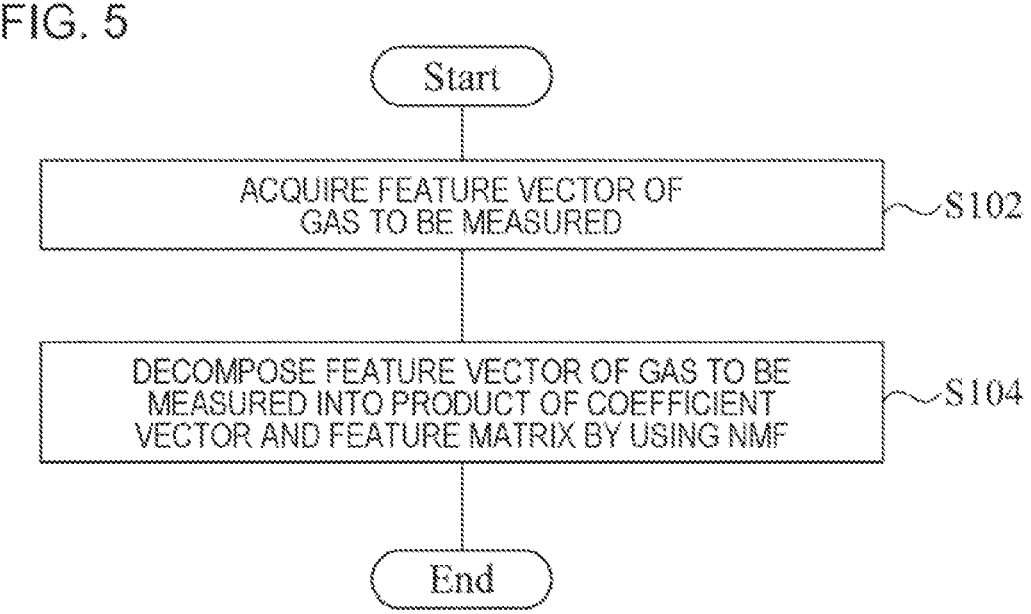
FIG. 5 is a flowchart illustrating a flow of a process executed by the information processing apparatus of Example Embodiment 1.

FIG. 5 is a flowchart illustrating a flow of a process executed by the information processing apparatus 2000 of Example Embodiment 1. The acquisition unit 2020 acquires the feature vector 20 of the gas to be measured (S102). The decomposition unit 2040 decomposes the feature vector 20 of gas to be measured into the product of the coefficient vector and the feature matrix by executing the NMF (S104).

<Acquisition of Feature Vector 20: S102>

The acquisition unit 2020 acquires the feature vector 20 of the gas to be measured. There are various methods of acquiring the feature vector 20. For example, the acquisition unit 2020 acquires the feature vector 20 by accessing the storage device in which the feature vector 20 is stored. This storage device may be provided inside the information processing apparatus 2000 or may be provided outside the information processing apparatus 2000. In addition, for example, the acquisition unit 2020 may acquire the feature vector 20 by receiving the feature vector 20 transmitted from another apparatus. This "another apparatus" is, for example, an apparatus that computes the feature vector 20 from the signal data 14 obtained from the sensor 10 for the gas to be measured.

<Execution of NMF: S104>

The decomposition unit 2040 decomposes the feature vector 20 into the coefficient vector and the feature matrix by executing the NMF on the feature vector 20 (S104). Various existing algorithms can be used as specific algorithms for the NMF.

How many feature vectors the feature vector 20 is decomposed into, that is, the number of columns of the feature matrix (=the number of elements of the coefficient vector) may or may not be set before executing the NMF. In the former case, the decomposition unit 2040 executes the NMF under the constraint condition that the number of elements of the coefficient vector and the number of columns of the feature vector are a predetermined number.

On the other hand, in the latter case, the decomposition unit 2040 executes the NMF without limiting the number of elements of the coefficient vector and the number of columns of the feature vector. Here, existing algorithms can be used as the NMF algorithm that is performed without such limitation. In this case, the number of columns in the feature matrix is determined as a result of executing the NMF, and the number of columns represents the number of components contained in the gas to be measured.

Note that, when the number of columns of the feature matrix is set in advance, the number of columns can be set by any method. For example, the number of columns in the feature matrix is given by user input. In addition, for example, the number of columns of the feature matrix may be fixedly set by the decomposition unit 2040 in advance.

<About Output of Processing Result>

The information processing apparatus 2000 outputs information (hereinafter, output information) indicating the result of a process by the decomposition unit 2040. There are various output modes of output information. For example, the information processing apparatus 2000 stores the output information in a storage device, displays the output information on a display device or transmits the output information to another apparatus.

The output information includes data representing the coefficient vector or the feature matrix. This data can be in various format data such as character string data and image data.

<About Feature Vector 20>

The feature vector 20 representing the feature of the gas to be measured is a vector 1) obtained by applying a predetermined process to the signal data 14 that is obtained by sensing the gas to be measured with the sensor 10, 2) in which the values of all the elements are equal to or greater than zero (non-negative), and 3) satisfying a condition of having linearity. As such a feature vector, for example, a vector representing various spectra obtained from the signal data 14 can be used.

For example, for the feature vector 20, a frequency spectrum representing the intensity of each of the plurality of frequency components included in the signal data 14 can be used. The frequency spectrum of the signal data 14 is obtained by subjecting the signal data 14 to a discrete Fourier transform.

In addition, for example, spectrum data related to various constants (hereinafter, feature constants) such as a velocity constant and a time constant obtained from the signal data 14 can be used for the feature vector 20. Hereinafter, the spectrum data of the feature constant will be described in detail.

First, the sensing in the sensor such as the sensor 10 that has a receptor to which a molecule is attached and outputs the detected value which is changed according to attachment and detachment of the molecule at the receptor can be modeled as follows.

(1) The sensor 10 is exposed to the gas to be measured containing K types of molecules.

(2) The concentration of each molecule k in the gas is a constant ρk.

(3) A total of N molecules can be adsorbed on the sensor 10.

(4) At time t, the number of molecules k attached to the sensor 10 is nk(t).

The time change of the number nk(t) of molecules k attached to the sensor 10 can be formulated as follows.

[Expression 2]

$$\frac{dn_k(t)}{dt} = \alpha_k \rho_k - \beta_k n_k(t) \quad (2)$$

The first and second terms on the right side in Expression (2) represent the amount of increase (the number of molecules k newly attached to the sensor 10) and the amount of decrease (the number of molecules k detached from sensor 10) of the molecules k per unit time, respectively. Further, αk is a velocity constant representing a velocity at which the molecule k is attached to the sensor 10, and βk is a velocity constant representing a velocity at which the molecule k is detached from the sensor 10.

Since the concentration ρk is constant, the number nk(t) of molecules k at time t can be formulated from the above Expression (2) as follows.

[Expression 3]

$$n_k(t) = n_k^* + (n_k(t_0) - n_k^*)e^{-\beta_k t} \quad (3)$$

$$\text{wherein, } n_k^* := \frac{\beta_k \rho_k}{\alpha_k}$$

Further, assuming that no molecule is attached to the sensor 10 at time t0 (initial state), nk(t) is represented as follows.

[Expression 4]

$$n_k(t) = n_k^*(1 - e^{-\beta_k t}) \quad (4)$$

The detected value of the sensor 10 is determined by a physical quantity related to viscoelasticity such as stress acting on the sensor 10 due to molecules contained in the gas and dynamic characteristics. It is considered that the physical quantity obtained from the sensor 10 due to a plurality of molecules can be represented by a conical combination of contributions of individual molecules to the physical quantity. However, the contribution of a molecule to a physical quantity is considered to differ depending on the type of molecule. That is, it can be said that the contribution of the molecule with respect to the detected value of the sensor 10 differs depending on the type of the molecule.

Thereby, the detected value y(t) of the sensor 10 can be formulated as follows.

[Expression 5]

$$y(t) = \sum_{k=1}^{K} \gamma_k n_k(t) \quad (5)$$

$$= \begin{cases} \xi_0 - \sum_{k=1}^{K} \xi_k e^{-\beta_k t} & \text{(when exposed to measurement target gas)} \\ \sum_{k=1}^{K} \xi_k e^{-\beta_k t} & \text{(when exposed to purge gas)} \end{cases}$$

$$\text{wherein, } \xi_k = \frac{\gamma_k \alpha_k \rho_k}{\beta_k} \quad (k = 1, \ldots, K), \xi_0 = \sum_{k=1}^{K} \xi_k$$

Both γk and ξk represent the contribution of the molecule k with respect to the detected value of the sensor 10.

Note that, the purge gas is a gas used to remove the influence of the gas to be measured from the sensor 10 and return the state of the sensor 10 to the initial state. As the signal data 14 obtained by measuring the gas to be measured by the sensor 10, not only the signal data obtained from the sensor 10 when the sensor 10 is exposed to the gas to be measured, but also the signal data obtained by exposing the sensor 10, after being exposed to the gas to be measured, to the purge gas can be used.

Here, when a set of feature constants Θ={θ1, θ2, ..., θm} is defined, the signal data 14 can be decomposed as shown in following Expression (6).

[Expression 6]

$$y(t) = \sum_{i=1}^{m} \xi_i f(\theta_i) \quad (6)$$

ξi is a contribution value representing the contribution of the feature constant θi with respect to the detected value of the sensor 10. Note that, the contribution ξ is zero for the feature constants corresponding to the components not contained in the sensed gas.

It can be said that the vector Ξ, which enumerates the contribution value ξ for a certain type of determined constant, represents the spectral data related to the feature constant in the signal data 14. Therefore, this vector Ξ can be used as the feature vector 20.

As the feature constant θ, the above-mentioned velocity constant β or the time constant τ, which is the reciprocal of the velocity constant, can be adopted. That is, the spectrum data related to the velocity constant β or the spectrum data related to the time constant τ obtained from the signal data 14 can be used as the feature vector 20. Note that, Expression (6) can be represented as follows for each of the cases where β and τ are used as θ.

[Expression 7]

$$y(t) = \sum_{i=1}^{m} \xi_i e^{-\beta_i t} \quad (7)$$

$$y(t) = \sum_{i=1}^{m} \xi_i e^{-t/\tau_i} \quad (8)$$

<<About Case where Feature Vector 20 can Include Negative Element>>

All elements of the vector decomposed by using the NMF need to be equal to or greater than zero. Therefore, when the feature vector can include a negative element, it is preferable that the decomposition unit 2040 performs preprocessing so that the element of the feature vector 20 does not include a negative value. For example, the preprocessing is a process of converting the negative element included in the feature vector 20 into the absolute value thereof or zero. Further, it is preferable that the decomposition unit 2040 performs post-processing for converting the sign to negative (multiply by −1) for each element obtained by decomposing the element converted from the negative value to an absolute value thereof in the preprocessing among the elements included in the feature matrix. For example, when the element on the j-th row of the feature vector 20 is converted from negative to the absolute value thereof, the decomposition unit 2040 converts the sign of each element on the j-th row of the feature matrix to negative.

Example Embodiment 2

The information processing apparatus 2000 of Example Embodiment 2 assumes a case where the feature vector is known for one or more components contained in the gas to be measured. For example, there is a case where the gas to be measured contains water vapor and the feature vector of water vapor is known. Even when a part of the components contained in the gas to be measured is known in this way, when the remaining components are unknown, it is useful to extract the feature vector of each component using the information processing apparatus 2000.

Therefore, in the information processing apparatus 2000 of Example Embodiment 2, the NMF is executed for the feature vector 20 of the gas to be measured, assuming that a part of feature vectors included in the feature matrix is known. That is, the decomposition unit 2040 of Example Embodiment 2 acquires information (hereinafter, premise information) indicating the feature vector for the component known to be contained in the gas to be measured, and executes the NMF for the feature vector 20 of the gas to be measured under the constraint condition that the feature vector is included in the feature matrix.

As a method for the acquisition unit 2020 to acquire the premise information, various methods can be adopted as in the method of acquiring the feature vector 20. However, the method of acquiring the premise information and the method of acquiring the feature vector 20 may be different from each other.

For example, it is assumed that the premise information shows the feature vector for k components, of the components contained in the gas to be measured. In this case, for example, in Expression (1) reprinted below, the NMF is executed after setting the feature vectors known from F1 to Fk in advance. As a result, the coefficient vector and the feature vector after F_k+1 are computed. Note that, as described above, αi>=0.

[Expression 8]

$$F_t = \sum_{1 \le i \le n} \alpha_i F_i \quad (1)$$

$$= \begin{pmatrix} \alpha_1 \\ \vdots \\ \alpha_n \end{pmatrix} (F_1 \quad \ldots \quad F_n)$$

Here, for a specific algorithm for executing the NMF under the constraint condition that one or more vectors that constitute a matrix obtained as a result is known, an algorithm for the NMF called a supervised NMF or a semi-supervised NMF can be used.

<Advantageous Effect>

With the information processing apparatus 2000 of the present example embodiment, when a part of components contained in the gas to be measured and the feature vectors thereof are known, by performing the NMF after setting feature vector in the feature matrix, the feature vectors of other components contained in the gas to be measured can be obtained. When a part of the matrix computed by the NMF is known in advance in this way, the number of searches performed by the NMF is reduced, and the time required to execute the NMF is shortened. Further, when a part of the matrix computed by using the NMF is known in advance, the accuracy of the NMF result (that is, the coefficient vector and the feature matrix) becomes high.

Therefore, with the information processing apparatus 2000 of the present example embodiment, by effectively utilizing the information related to the components known in advance, the coefficient vector and the feature matrix can be computed accurately while shortening the time required for the process for obtaining the coefficient vector and the feature matrix.

<Example of Functional Configuration>

The functional configuration of the information processing apparatus 2000 of Example Embodiment 2 is represented by, for example, FIG. 3 in the same manner as the functional configuration of the information processing apparatus 2000 of Example Embodiment 1. However, the decomposition unit 2040 of Example Embodiment 2 acquires the premise information and executes the NMF on the feature vector 20 under the constraint condition that the feature vector shown in the premise information is included in the feature matrix obtained by the NMF.

<Example of Hardware Configuration>

The hardware configuration of the computer that implements the information processing apparatus 2000 of Example Embodiment 2 is represented by, for example, FIG. 4 as in Example Embodiment 1. However, in the storage device 1080 of the computer 1000 that implements the information processing apparatus 2000 of the present example embodiment, a program module that implements the functions of the information processing apparatus 2000 of the present example embodiment is stored.

<Process Flow>

Figure 6:
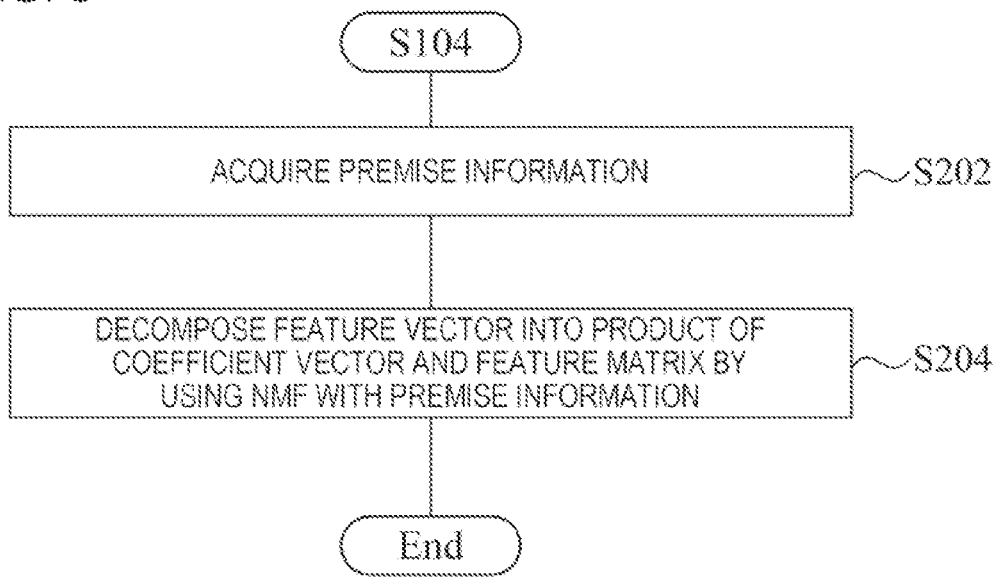
FIG. 6 is a flowchart illustrating a flow of a process executed by a decomposition unit of Example Embodiment 2.

FIG. 6 is a flowchart illustrating a flow of a process executed by the decomposition unit 2040 of Example Embodiment 2. The flowchart represents the process performed in S104 in FIG. 5. The decomposition unit 2040 acquires the premise information (S202). The decomposition unit 2040 executes the NMF on the feature vector 20 using the premise information (S204).

<Modification Example>

The decomposition unit 2040 may execute the NMF after setting each feature vector shown in the premise information in the feature matrix and allowing the feature vector to be changed to some extent. Specifically, the decomposition unit 2040 executes the basis conversion type supervised NMF after setting the feature vector shown in the premise information as the initial value of the column vector of the feature matrix. In the basis conversion type supervised NMF, a known vector is set as the initial value of a part of the matrix obtained as a result of the NMF, but the change of the vector set as the initial value in this way is allowed. As a specific algorithm of the basis conversion type supervised NMF, a known one can be used.

The signal data 14 obtained by sensing the gas with the sensor 10 is affected by the measurement environment such as temperature or noise. Therefore, even when a component having a known feature vector is contained in the gas to be measured, the feature vector of the component does not always completely match the known data. Therefore, by using the basis conversion type supervised NMF that allows the change of the vector set as the initial value as described above, the coefficient vector and the feature matrix can be obtained from the feature vector 20 of the gas to be measured in consideration of the fluctuation of the feature vector due to the influence of such a measurement environment or noise. Therefore, the conical combination coefficient and the feature vector of each component contained in the gas to be measured can be computed with higher accuracy.

Regarding the known feature vector, the premise information may further include information indicating how much the feature vector is allowed to be deformed. For example, by performing a test on a certain component under various measurement environments and computing a feature vector, the degree of fluctuation of the feature vector of that component is recognized. As a specific example, the average vector $\mu$ and the standard deviation $\sigma$ of the distance from the average vector $\mu$ are computed for a plurality of feature vectors obtained in the test. Thereafter, the premise information includes the average vector $\mu$ as the feature vector of the component and includes a value such as the standard deviation $\sigma$ itself or a constant multiple ($2\sigma$, $3\sigma$, or the like) thereof as an index value (hereinafter, the allowable index value) representing a range in which deformation is allowed for the feature vector.

In this case, the decomposition unit 2040 applies the average vector $\mu$ shown in the premise information as the initial value of the feature matrix and executes the NMF under the constraint condition that the distance from the initial value is equal to or less than the allowable index value. By doing so, it is possible to allow the deformation for the known feature vector and prevent the deformation from becoming excessively large.

Example Embodiment 3

Figure 7:
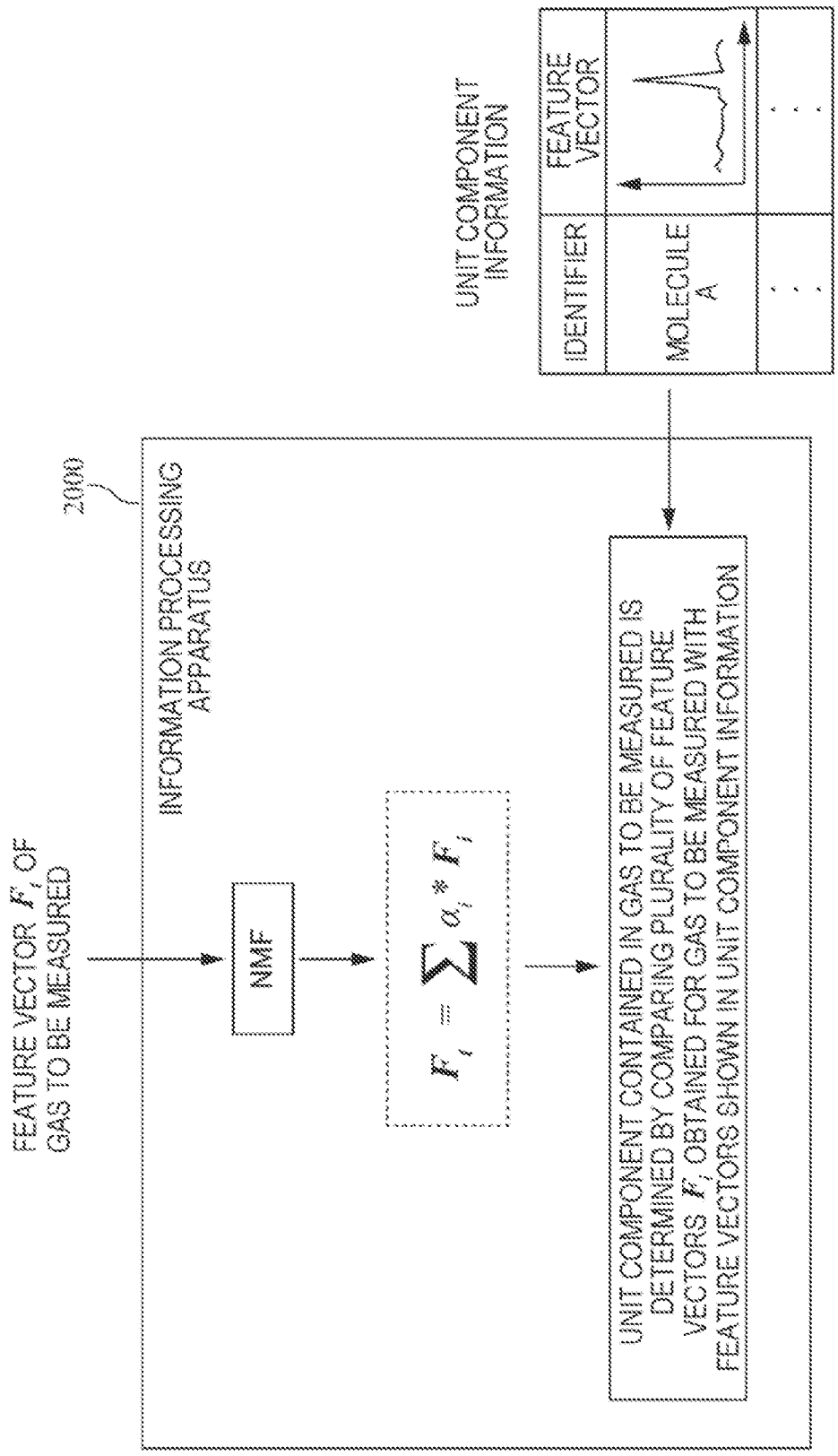
FIG. 7 is a diagram illustrating an outline of an information processing apparatus according to Example Embodiment 3.

FIG. 7 is a diagram illustrating an outline of the information processing apparatus 2000 of Example Embodiment 3. The information processing apparatus 2000 of Example Embodiment 3 determines one or more unit components contained in the gas to be measured, by using the feature matrix obtained by the decomposition unit 2040. The unit component is, for example, a single type of molecule. In addition, for example, a unit component is a combination of molecules that produce a determined odor. For example, the unit component that produces the odor of apple is a combination of molecules that produce the odor of apple (that is, a combination of molecules contained in gas produced from apple).

The information processing apparatus 2000 determines something similar to the feature vector of a known unit component from among the feature vectors included in the feature matrix obtained by the decomposition unit 2040. When the feature vector included in the feature matrix is similar to the feature vector of a certain unit component, the information processing apparatus 2000 determines the unit component as the unit component included in the gas to be measured.

In order to implement such a process, information representing a feature vector for each of the known unit components is prepared in advance. This information is called unit component information. The unit component information is information in which the identifier of the unit component and the feature vector of the unit component are associated with each other. The feature vector of the unit component is, for example, a feature vector computed for signal data obtained by sensing gas containing only the unit component with the sensor 10.

The decomposition unit 2040 compares each of the plurality of feature vectors included in the feature matrix with each feature vector shown in the unit component information. As a result, the decomposition unit 2040 determines a feature vector similar to the feature vector included in the feature matrix from the unit component information and determines the unit component having the identifier corresponding to the determined feature vector as the unit component contained in the gas to be measured.

Further, the information processing apparatus 2000 may determine the conical combination coefficient of the determined unit component in the gas to be measured based on the coefficient vector. For example, when it is determined that the feature vector in the i-th column of the feature matrix is similar to the feature vector of the unit component X, the decomposition unit 2040 determines the value of the i-th element of the coefficient vector as the conical combination coefficient of the unit component X in the gas to be measured.

<Advantageous Effect>

With the information processing apparatus 2000 of the present example embodiment, for the feature vector included in the feature matrix obtained by decomposing the feature vector 20 by using the NMF, the unit component contained in the gas to be measured is determined by determining the feature vector of a known unit component similar to the feature vector. Therefore, with the information processing apparatus 2000, it is possible to easily recognize what kind of component is contained in the gas to be measured from the feature vector 20 of the gas to be measured.

<Example of Functional Configuration>

Figure 8:
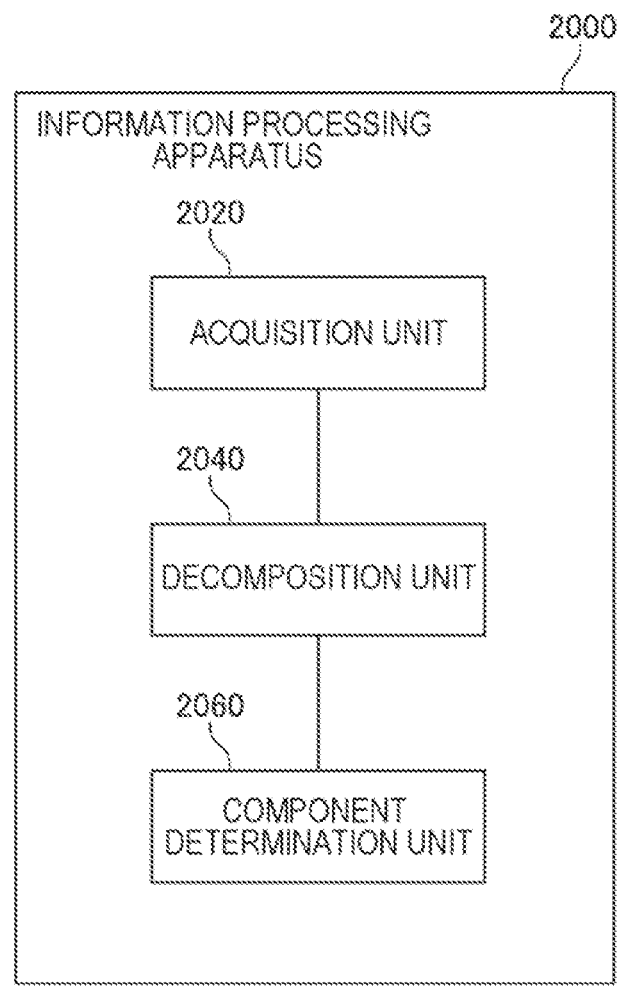
FIG. 8 is a block diagram illustrating a functional configuration of the information processing apparatus according to Example Embodiment 3.

FIG. 8 is a block diagram illustrating the functional configuration of the information processing apparatus 2000 of Example Embodiment 3. The information processing apparatus 2000 of Example Embodiment 3 has a component determination unit 2060 in addition to the acquisition unit 2020 and the decomposition unit 2040. The component determination unit 2060 determines a feature vector similar to the vector included in the feature matrix obtained by the decomposition unit 2040 from the unit component information and determines the unit component corresponding to the determined feature vector as the unit component contained in the gas to be measured.

<Example of Hardware Configuration>

The hardware configuration of the computer that implements the information processing apparatus 2000 of Example Embodiment 3 is represented by, for example, FIG. 4 as in Example Embodiment 1. However, in the storage device 1080 of the computer 1000 that implements the information processing apparatus 2000 of the present example embodiment, a program module that implements the functions of the information processing apparatus 2000 of the present example embodiment is stored.

<Process Flow>

Figure 9:
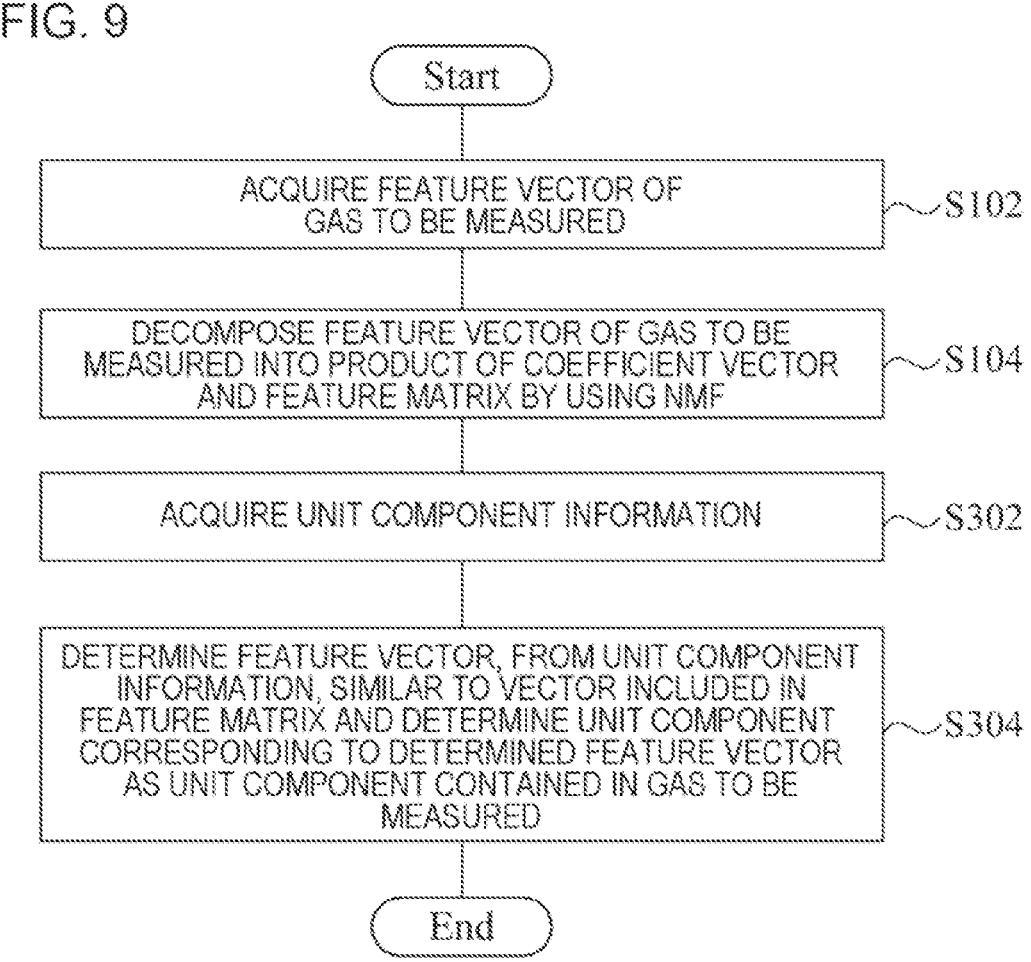
FIG. 9 is a flowchart illustrating a flow of a process executed by the information processing apparatus of Example Embodiment 3.

FIG. 9 is a flowchart illustrating a flow of a process executed by the information processing apparatus 2000 of Example Embodiment 3. S102 and S104 in FIG. 9 are the same as S102 and S104 in FIG. 5, respectively. After S104, the component determination unit 2060 acquires the unit component information (S302). The component determination unit 2060 determines a feature vector similar to the vector included in the feature matrix from the unit component information and determines the unit component corresponding to the determined feature vector as the unit component contained in the gas to be measured (S304).

<About Unit Component Information>

As described above, the unit component information is information in which the identifier of the unit component and the feature value of the unit component are associated with each other. It is assumed that the unit component is a single type of molecule. In this case, the unit component information associates the identifier of the molecule with the feature vector of the molecule. The identifier of a molecule is the name or chemical formula of the molecule. The feature vector of a molecule is a feature vector obtained from signal data obtained by sensing gas containing only the molecule with the sensor 10. Note that, it is assumed that the unit component information is stored in advance in the storage device provided inside or outside the information processing apparatus 2000.

It is assumed that the unit component is a combination of molecules that produce a determined odor. In this case, the identifier of the unit component indicated by the unit component information is, for example, the name of an odor (hereinafter it is referred to as an odor label). Further, the feature vector of the unit component is a feature vector of the gas determined by the odor label.

Here, the "determined odor" is an odor produced from a determined substance, such as "odor of apple" or "odor of liquor". Note that, the substance is not limited to food, and can be any substance such as machinery, building materials, chemicals, mold, charred, or kitchen waste. In this case, the odor label is the name of the substance that emits the odor or the like.

Further, the "determined odor" may be an odor associated with an abstract concept such as the place or situation where the odor is smelled, such as "odor of cafe", "odor of pool", "odor of green", "odor of closet", "sweet odor", "fishy odor", or "rainy day odor". In this case, the odor label is a word that represents such an abstract concept (for example, a place type or name, a word that represents a situation, or the like).

Figure 10:
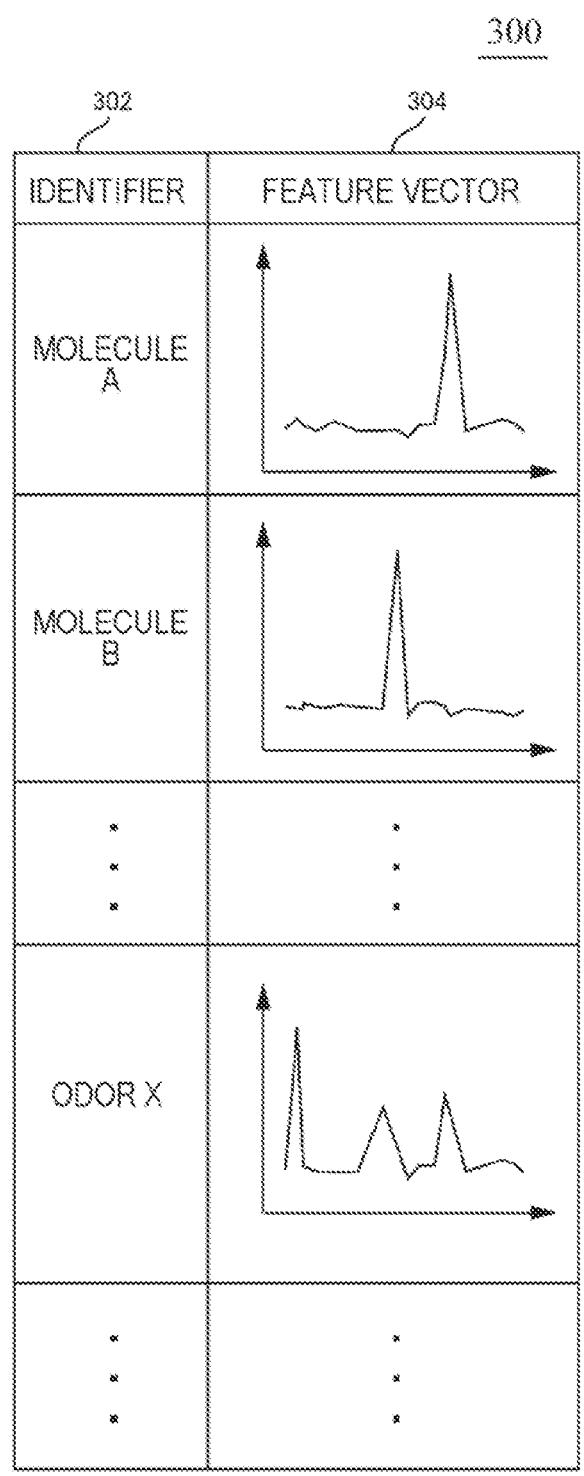
FIG. 10 is a diagram illustrating unit component information in a table format.

FIG. 10 is a diagram illustrating unit component information in a table format. The table in FIG. 10 is called a table 300. The table 300 has two columns, an identifier 302 and a feature vector 304. Each record in the table 300 associates the feature vector shown in the feature vector 304 with the identifier of the unit component shown in the identifier 302. The identifier 302 represents an identifier of a molecule or an odor label.

<Comparison Between Feature Vectors>

The decomposition unit 2040 determines whether or not the feature vector included in the feature matrix and the feature vector indicated by the unit component information are similar. For example, the decomposition unit 2040 computes the degree of similarity between the feature vectors. Thereafter, the decomposition unit 2040 determines that the compared feature vectors are similar to each other when the computed similarity is equal to or higher than a predetermined value. This predetermined value is stored in a storage device accessible from the decomposition unit 2040.

For a certain feature vector A included in the feature matrix, there may be a plurality of feature vectors of unit components whose similarity is equal to or higher than a threshold value. In this case, for example, the component determination unit 2060 determines the unit component having the maximum similarity as the unit component corresponding to the feature vector A. In addition, for example, the component determination unit 2060 may determine each of the plurality of unit components having a similarity of a predetermined value or more as a unit component that may contain the gas to be measured.

The similarity between the two feature vectors to be compared can be represented, for example, by using the distance between the vectors. Various norms, such as the L1 norm and the L2 norm, can be used for the distance between the vectors.

<About Output of Determined Result>

The information processing apparatus 2000 outputs information (hereinafter, second output information) representing a unit component contained in the gas to be measured. For example, the second output information is text data or image data indicating an identifier of each unit component contained in the gas to be measured and a conical combination coefficient thereof. In addition, for example, the second output information may be graphical information in which an identifier of each unit component contained in the gas to be measured and a conical combination coefficient thereof are represented by a table or a graph.

Figure 11:
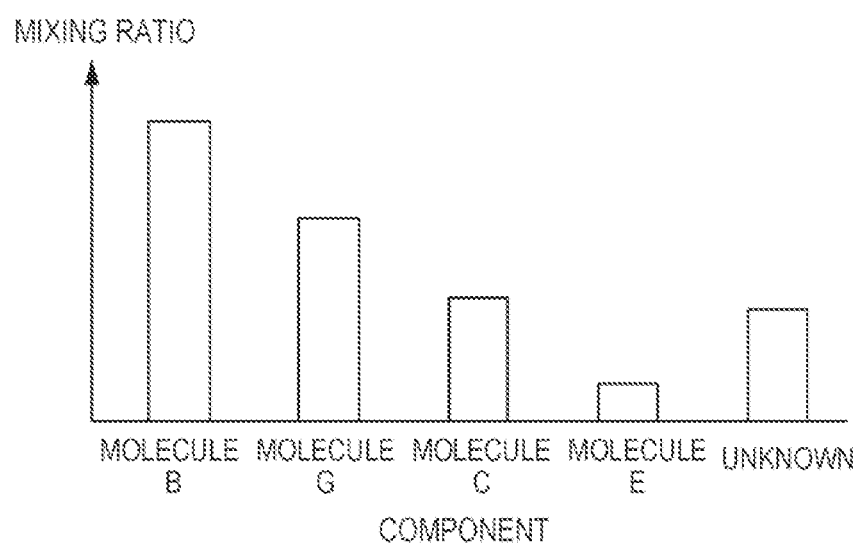
FIG. 11 is a graph representing unit components contained in gas to be measured.

FIG. 11 is a graph representing unit components contained in gas to be measured. In this example, the NMF is executed under the condition that the total sum of the conical combination coefficients is 1 so that the conical combination coefficients represent the mixing ratio. In the graph, the horizontal axis shows the name of each molecule contained in the gas to be measured, and the vertical axis shows the mixing ratio of each molecule. It is assumed that the decomposition unit 2040 computes a feature matrix having five feature vectors from the feature vector 20 of the gas to be measured. Further, of these five feature vectors, it is assumed that the four feature vectors are determined to be similar to the feature vectors of the molecules B, C, E, and G, respectively. That is, it is assumed that the gas to be measured is determined to contain molecules B, C, E, and G.

From this result, the molecules B, C, E, and G are shown in the graph shown in FIG. 11. Further, the mixing ratio of these molecules (that is, the values of the elements of the coefficient vector corresponding to these feature vectors) is shown as the values on the vertical axis of these molecules. Of the feature vectors included in the feature matrix, the corresponding unit component of one feature vector is unknown. Therefore, the graph in FIG. 11 shows the label "Unknown". Note that, in this graph, the unit components are sorted in descending order of the mixing ratio. However, those whose components are unknown are shown at the end.

By outputting the components of the gas to be measured as graphical information in this way, a user of the information processing apparatus 2000 can intuitively and easily understand the components of the gas to be measured.

<Usage Example of Result of Determined Component>

The results of determining the components contained in the gas to be measured can be used for various purposes. For example, when performing a discriminant analysis on a feature value obtained from the gas to be measured, the result of a process by the component determination unit 2060 can be used. Specifically, before performing the discriminant analysis on the feature vector 20 of the target gas, it is possible to remove the feature vector of an extra component that lowers the accuracy of the discriminant analysis.

For example, soft drinks and alcohol often contain a large amount of water. In this case, when the feature vectors of vapor of these drinks are compared as they are, the influence of the common term of the feature vector of water vapor is large, and it is difficult to make a highly accurate comparison.

Therefore, it is preferable that the feature vector 20 of the gas to be measured representing the vapor of the drink is decomposed into a plurality of feature vectors using the information processing apparatus 2000, the feature vector of water vapor is determined from among the plurality of feature vectors, and the discriminant analysis is performed after removing the feature vector of the water vapor. By doing so, it becomes possible to compare components other than water, that is, to compare between distinctive components of each drink, and the accuracy of discriminant analysis is improved.

Although the example embodiments of the present invention have been described above with reference to the drawings, these are examples of the present invention, and a configuration in which the above example embodiments are combined or various configurations other than the above can be adopted.

The whole or part of the example embodiments disclosed above can be described as, but not limited to, the following supplementary notes.

1. An information processing apparatus including: an acquisition unit that acquires a feature vector of gas to be measured which is obtained based on signal data of a detected value of a sensor that senses the gas to be measured; and a decomposition unit that decomposes the feature vector of the gas to be measured into a product of a vector and a matrix by using a non-negative matrix factorization (NMF), in which the detected value of the sensor changes according to an attachment and a detachment of a molecule contained in a sensed gas, and a value of each element of the feature vector of the gas to be measured is equal to or greater than zero.

2. The information processing apparatus according to 1., in which the decomposition unit acquires a feature vector of a component contained in the gas to be measured and executes the NMF on the feature vector of the gas to be measured under a condition that the acquired feature vector is included in the matrix.

3. The information processing apparatus according to 1., in which the decomposition unit acquires a feature vector of a component contained in the gas to be measured, sets an initial value of a vector in the matrix to the acquired feature vector, and then executes a basis conversion type supervised NMF on the feature vector of the gas to be measured.

4. The information processing apparatus according to any one of 1. to 3., further including: a component determination unit that determines, from unit component information where a unit component and a feature vector of the unit component are associated with each other, the feature vector similar to a vector included in the matrix obtained by the decomposition unit, and determines the unit component corresponding to the determined feature vector as a unit component contained in the gas to be measured.

5. The information processing apparatus according to 4., in which the component determination unit determines an element corresponding to the feature vector of the unit component contained in the gas to be measured among elements of the vector obtained by the decomposition unit, as a conical combination coefficient of the unit component in the gas to be measured.

6. The information processing apparatus according to any one of 1. to 5., in which the feature vector of the gas to be measured represents a frequency spectrum of the signal data of the detected value obtained from the sensor that senses the gas to be measured.

7. The information processing apparatus according to any one of 1. to 6., in which the feature vector of the gas to be measured represents a magnitude of contribution of each of a plurality of feature constants with respect to the signal data of the detected value obtained from the sensor that senses the gas to be measured, and the feature constant is a time constant or a velocity constant related to a magnitude of a time change in the amount of molecules attached to the sensor.

8. A control method executed by a computer, the method including: an acquisition step of acquiring a feature vector of gas to be measured obtained based on signal data of a detected value of a sensor that senses the gas to be measured; and a decomposition step of decomposing the feature vector of the gas to be measured into a product of a vector and a matrix by using a non-negative matrix factorization (NMF), in which the detected value of the sensor changes according to an attachment and a detachment of a molecule contained in a sensed gas, and a value of each element of the feature vector of the gas to be measured is equal to or greater than zero.

9. The control method according to 8., in which in the decomposition step, a feature vector of a component contained in the gas to be measured is acquired, and the NMF is executed on the feature vector of the gas to be measured under a condition that the acquired feature vector is included in the matrix.

10. The control method according to 8., in which in the decomposition step, a feature vector of a component contained in the gas to be measured is acquired, and an initial value of a vector in the matrix is set to the acquired feature vector and then a basis conversion type supervised NMF is executed on the feature vector of the gas to be measured.

11. The control method according to any one of 8. to 10., further including: a component determination step of determining, from unit component information where a unit component and a feature vector of the unit component are associated with each other, the feature vector similar to a vector included in the matrix obtained by the decomposition step, and determining the unit component corresponding to the determined feature vector as a unit component contained in the gas to be measured.

12. The control method according to 11., in which in the component determination step, an element corresponding to the feature vector of the unit component contained in the gas to be measured is determined among elements of the vector obtained by the decomposition step, as a conical combination coefficient of the unit component in the gas to be measured.

13. The control method according to any one of 8. to 12., in which the feature vector of the gas to be measured represents a frequency spectrum of the signal data of the detected value obtained from the sensor that senses the gas to be measured.

14. The control method according to any one of 8. to 13., in which the feature vector of the gas to be measured represents a magnitude of contribution of each of a plurality of feature constants with respect to the signal data of the detected value obtained from the sensor that senses the gas to be measured, and the feature constant is a time constant or a velocity constant related to a magnitude of a time change in the amount of molecules attached to the sensor.

15. A program that causes a computer to execute each step of the control method according to any one of 8. to 14.

What is claimed is:

1. An information processing apparatus comprising:
a processor; and
a memory storing instructions executable by the processor to:
acquire a gas feature vector of a gas obtained based on signal data of a detected value of a sensor that senses the gas, the gas feature vector to be decomposed into a product of a coefficient vector and a matrix;
acquire a component feature vector of a component contained in the gas;
set an initial value of one constituent vector of the matrix to the component feature vector;
decompose the gas feature vector into the product of the coefficient vector and the matrix by executing basis conversion-type supervised non-negative matrix factorization (NMF) on the gas feature vector;
determine, from unit component information where a unit component and a feature vector of the unit component are associated with each other, the feature vector similar to a vector included in the matrix, and determine the unit component corresponding to the determined feature vector as a unit component contained in the gas; and
output the determined unit component to a display device, wherein
the detected value of the sensor changes according to an attachment and a detachment of a molecule contained in the gas,
a value of each of a plurality of elements of the gas feature vector is equal to or greater than zero, and
setting the initial value of the one constituent vector of the matrix to the component feature vector provides for higher accuracy in computing a component feature vector of each of a plurality of other components contained in the gas based on the detected value of the sensor.

2. The information processing apparatus according to claim 1, wherein
the processor acquires the component feature vector of the component contained in the gas and executes the basis conversion-type supervised NMF on the gas feature vector under a condition that the component feature vector is included in the matrix.

3. The information processing apparatus according to claim 1, wherein
the processor determines an element corresponding to the feature vector as the unit component contained in the gas among elements of the vector, as a conical combination coefficient of the unit component in the gas.

4. The information processing apparatus according to claim 1, wherein
the gas feature vector represents a frequency spectrum of the signal data of the detected value obtained from the sensor that senses the gas.

5. The information processing apparatus according to claim 1, wherein
the gas feature vector represents a magnitude of contribution of each of a plurality of feature constants with respect to the signal data of the detected value obtained from the sensor that senses the gas, and
the feature constant is a time constant or a velocity constant related to a magnitude of a time change in an amount of molecules attached to the sensor.

6. A control method executed by a computer, the method comprising:
acquiring a gas feature vector of gas obtained based on signal data of a detected value of a sensor that senses the gas, the gas feature vector to be decomposed into a product of a coefficient vector and a matrix;
acquiring a component feature vector of a component contained in the gas;
setting an initial value of one constituent component of the matrix to the component feature vector;
decomposing the gas feature vector into the product of the coefficient vector and the matrix by executing basis conversion-type supervised non-negative matrix factorization (NMF) on the gas feature vector;
determining, from unit component information where a unit component and a feature vector of the unit component are associated with each other, the feature vector similar to a vector included in the matrix, and determining the unit component corresponding to the determined feature vector as a unit component contained in the gas; and
outputting the determined unit component to a display device, wherein
the detected value of the sensor changes according to an attachment and a detachment of a molecule contained in the gas,
a value of each of a plurality of elements of the gas feature vector is equal to or greater than zero, and
setting the initial value of the one constituent vector of the matrix to the component feature vector provides for higher accuracy in computing a component feature vector of each of a plurality of other components contained in the gas based on the detected value of the sensor.

7. The control method according to claim 6, wherein
the component feature vector of the component contained in the gas is acquired, and the basis conversion-type supervised NMF is executed on the gas feature vector under a condition that the component feature vector is included in the matrix.

8. The control method according claim 6, further comprising:
determining, from unit component information where a unit component and a feature vector of the unit component are associated with each other, the feature vector similar to a vector included in the matrix, and determining the unit component corresponding to the determined feature vector as a unit component contained in the gas.

9. The control method according to claim 8, wherein
an element corresponding to the feature vector of the unit component contained in the gas is determined among elements of the vector, as a conical combination coefficient of the unit component in the gas.

10. The control method according to claim 6, wherein
the gas feature vector represents a frequency spectrum of the signal data of the detected value obtained from the sensor that senses the gas.

11. The control method according to claim 6, wherein
the gas feature vector of the gas represents a magnitude of contribution of each of a plurality of feature constants with respect to the signal data of the detected value obtained from the sensor that senses the gas, and
the feature constant is a time constant or a velocity constant related to a magnitude of a time change in an amount of molecules attached to the sensor.

12. A non-transitory storage medium storing a program that causes a computer to execute a control method, the control method comprising:
acquiring a gas feature vector of gas obtained based on signal data of a detected value of a sensor that senses the gas, the gas feature vector to be decomposed into a product of a coefficient vector and a matrix;
acquiring a component feature vector of a component contained in the gas;
setting an initial value of one constituent component of the matrix to the component feature vector;
decomposing the gas feature vector into the product of the coefficient vector and the matrix by executing basis conversion-type supervised non-negative matrix factorization (NMF) on the gas feature vector;
determining, from unit component information where a unit component and a feature vector of the unit component are associated with each other, the feature vector similar to a vector included in the matrix, and determining the unit component corresponding to the determined feature vector as a unit component contained in the gas; and
outputting the determined unit component to a display device, wherein
the detected value of the sensor changes according to an attachment and a detachment of a molecule contained in the gas,
a value of each of a plurality of elements of the gas feature vector is equal to or greater than zero, and
setting the initial value of the one constituent vector of the matrix to the component feature vector provides for higher accuracy in computing a component feature vector of each of a plurality of other components contained in the gas based on the detected value of the sensor.

13. The information processing apparatus according to claim 1, wherein
the processor outputs a graph representing a ratio of a plurality of unit components, including the determined unit component, contained in the gas.

14. The information processing apparatus according to claim 1, wherein
the gas contains water vapor,
the processor acquires a feature vector of the water vapor as the component feature vector of the component, and
the processor determines the unit component containing the water vapor and outputs the determined unit component.

* * * * *